(12) United States Patent
Burren et al.

(10) Patent No.: US 7,771,399 B2
(45) Date of Patent: Aug. 10, 2010

(54) INJECTION DEVICE WITH DOSE METERING MECHANISM WITH MULTIPLE ANTI-ROTATION LOCKING SYSTEM

(75) Inventors: Stefan Burren, Bremgarten (CH); Ulrich Moser, Heimiswil (CH); Christian Schrul, Burgdorf (CH); Christoph Sommer, Ramsei (CH)

(73) Assignee: TecPharma Licensing AG, Burgdorf (CH)

( * ) Notice: Subject to any disclaimer, the term of this patent is extended or adjusted under 35 U.S.C. 154(b) by 965 days.

(21) Appl. No.: 11/550,998

(22) Filed: Oct. 19, 2006

(65) Prior Publication Data

US 2007/0167921 A1 Jul. 19, 2007

Related U.S. Application Data

(63) Continuation of application No. PCT/CH2005/000217, filed on Apr. 19, 2005.

(30) Foreign Application Priority Data

Apr. 23, 2004 (DE) ............... 20 2004 006 611 U

(51) Int. Cl.
*A61M 5/00* (2006.01)
(52) U.S. Cl. ............... 604/211; 604/207; 604/208; 604/218; 604/224; 606/566; 606/567
(58) Field of Classification Search ............ 604/68, 604/71–72, 156, 181, 183, 187, 188, 193, 604/195–196, 207, 208, 211, 218, 224, 232; 128/919; 600/566–567
See application file for complete search history.

(56) References Cited

U.S. PATENT DOCUMENTS 5,304,152 A * 4/1994 Sams ............... 604/207

| 5,591,136 | A | * | 1/1997 | Gabriel ............... 604/211 |
| 5,743,889 | A | * | 4/1998 | Sams ............... 604/211 |
| 5,807,346 | A | * | 9/1998 | Frezza ............... 604/208 |
| 6,086,567 | A | * | 7/2000 | Kirchhofer et al. ............... 604/211 |
| 6,221,046 | B1 | * | 4/2001 | Burroughs et al. ............... 604/153 |
| 6,235,004 | B1 | * | 5/2001 | Steenfeldt-Jensen et al. ..... 604/207 |
| 6,277,101 | B1 | * | 8/2001 | Kirchhofer et al. ............... 604/232 |
| 6,562,006 | B1 | * | 5/2003 | Hjertman et al. ............... 604/208 |
| 7,169,132 | B2 | * | 1/2007 | Bendek et al. ............... 604/208 |

(Continued)

FOREIGN PATENT DOCUMENTS

EP 0611035 8/1994

*Primary Examiner*—Nicholas D Lucchesi
*Assistant Examiner*—Quynh-Nhu H Vu
(74) *Attorney, Agent, or Firm*—Dorsey & Whitney LLP; David E. Bruhn, Esq.

(57) ABSTRACT

A drive and dosing module for an injection device, and an injection device including the module, wherein the module includes a dosing member which can be displaced into one of several dosing positions in relation to a drive member to set a product dose, wherein one of the dosing or drive members forms several dosing stops at axially different heights and rotational stops that are associated with the dosing stops and the other member forms at least one selection element, and wherein the drive member can be moved in relation to the dosing member until it reaches a trigger position in which the at least one selection element attains one of the dosing stops and, in said trigger position, the selection element and the rotational stops combine to lock the rotation of the dosing member in both directions.

14 Claims, 9 Drawing Sheets

U.S. PATENT DOCUMENTS

| | | |
|---|---|---|
| 7,377,913 B2 * | 5/2008 | Gurtner ............... 604/211 |
| 7,553,299 B2 * | 6/2009 | Veasey et al. ........... 604/208 |
| 2001/0009990 A1 | 7/2001 | Hostettler et al. |
| 2002/0016571 A1 * | 2/2002 | Kirchhofer et al. ......... 604/218 |
| 2003/0158523 A1 | 8/2003 | Hjertman et al. |
| 2004/0112925 A1 | 6/2004 | Py et al. |
| 2004/0127858 A1 | 7/2004 | Bendek |

* cited by examiner

INJECTION DEVICE WITH DOSE METERING MECHANISM WITH MULTIPLE ANTI-ROTATION LOCKING SYSTEM

CROSS-REFERENCE TO RELATED APPLICATIONS

This application is a continuation of International Patent Application No. PCT/CH2005/00217, filed on Apr. 19, 2005, which claims priority to German Application No. 20 2004 006 611.4, filed on Apr. 23, 2004, the contents of both of which are hereby incorporated in their entirety by reference herein.

BACKGROUND

The invention relates to devices for delivering, administering, injection, dispensing or infusing substances, and to methods of making and using such devices. More particularly, it relates to a dose metering mechanism with a multiple anti-rotation locking system and a device for administering an injectable product, which enable a dose to be freely selected by a user of the device. The injection device is particularly suitable for applications where the user self-administers the product and is able to select, i.e. set or choose, the dose individually with every administration. In some preferred embodiments, the device is an injection device of the type used for administering insulin as a diabetic treatment, or for administering growth hormone.

Patent specification EP 0 713 403 A1 discloses a syringe for administering liquid pharmaceutical mixtures and generally also other liquids, which allows a dose of liquid to be administered per injection to be set once. Specifically, a setting is made by a pharmacist. However, in the case of a patient who then has to self-administer the pharmaceutical liquid with the syringe, it is difficult to change the dose, once it has been set. The intention is to prevent an incorrect dose from being administered with the syringe. A syringe of this type is not entirely satisfactory for all uses because in some treatment regimes, an optimum dose varies depending, for example, on the time of day, sporting activities or the consumption of meals.

Injection devices which satisfy the need for variable doses or dosing are known from patent specifications WO 97/36625 and DE 199 00 792 C2, for example. These two specifications relate to injection devices, each of which has a conveying mechanism for dispensing the product, and a dose metering mechanism for setting the product dose which can be conveyed and hence dispensed by the conveying device during a subsequent injection. The conveying mechanism comprises a plunger, the forward stroke of which conveys the product from a product reservoir, a plunger rod and a drive member for the plunger rod. The drive member and the plunger rod engage with one another so that a forward movement of the drive member causes the plunger rod to move in the same way but the drive member performs a reverse movement in the opposite direction until it reaches a trigger position, from which another injection can be initiated. The trigger position is determined by means of the dose metering mechanism, which forms an adjustable dose setting stop for the drive member. Although the known devices have proved to be efficient in practice, they could still be improved to make them more reliable in terms of ruling out the risk of incorrect doses.

Patent specification EP 0 879 610 B1 discloses a re-usable dispensing mechanism for medicaments. A projection mounted on the housing of the device engages in one of several grooves adapted to the projection, disposed on a selection element. The projection is resiliently attached to the housing so that when the housing is turned towards the selection element, the selection element springs out of one groove into an adjacent groove, thereby making an audible clicking sound.

SUMMARY

One objective of the present invention is to provide a drive and dose metering module and an injection device for administering an injectable product, which enable a dose to be freely selected while reducing the risk of incorrect dosage.

In one embodiment, the present invention comprises a drive and dosing module for an injection device, and an injection device comprising the module, wherein the module includes a dosing member which can be displaced into one of several dosing positions in relation to a drive member to set a product dose, wherein one of the dosing or drive members forms several dosing stops at axially different heights and rotational stops that are associated with the dosing stops and the other member forms at least one selection element, and wherein the drive member can be moved in relation to the dosing member until it reaches a trigger position in which the at least one selection element attains one of the dosing stops and, in said trigger position, the selection element and the rotational stops combine to lock the rotation of the dosing member in both directions.

In one embodiment, the present invention relates to an injection device for administering an injectable product, wherein the device is portable and can be carried in a pocket, e.g., the type of device known as an injection pen. The injection device comprises a housing with a reservoir for the product, a conveying mechanism for conveying the product and a dose metering mechanism enabling a product dose to be freely selected for every injection. The housing itself may constitute the reservoir. However, the housing may be designed as a housing compartment for a product container which may be of the type sold as standard in the form of a pre-filled ampoule. The expression "housing with a reservoir" should also generally be interpreted as meaning a housing which forms a housing compartment for a product container in which the product container has not yet been inserted.

In some embodiments, the conveying mechanism is mounted, so that it can be moved, by a mechanism holder, which may be a housing portion. It may perform a conveying motion by which the product is conveyed out of the reservoir and dispensed. It can be moved relative to the housing or at least a part of the housing into at least two, and in some embodiments, exactly two, different positions which are pre-defined by stops. One of the positions is a triggering position from which the conveying movement is performed directly or after firstly performing another movement. The other position is a release position, from which the conveying mechanism can be moved into the triggering position.

In some embodiments, the conveying movement and the movement into the triggering position are linear movements, and in some embodiments, may take place along a single translation axis. The movement out of the release position into the triggering position may be in exactly the opposite direction from the conveying movement. The conveying mechanism is able to move backwards and forwards between the triggering position and the release position, and, in some embodiments, moves exclusively in this manner. The movement out of the triggering position may be initiated by manual pressure on the conveying mechanism and the movement into the triggering position may be activated by manually applied tension. To simplify matters, the movement into the triggering position will be referred to as the re-setting movement. The fact that the conveying mechanism performs a movement does not mean, in the case of one preferred multi-part design of the conveying mechanism, that all parts of the conveying mechanism always perform the movement in question or that they perform a joint movement at all, although a joint movement is preferred in at least certain phases and/or embodiments.

In some embodiments, the dose metering mechanism is mounted, e.g., connected, to said mechanism holder, so that it is able to perform a dose metering movement relative to the conveying mechanism or at least a part of the conveying mechanism, to set or select the product dose to be conveyed by the conveying mechanism. The product dose which can be set is pre-defined by dose positions, into which the dose metering mechanism releaseably moves or latches during the dose metering movement. The corresponding latched engagement may be formed by the housing or/and the conveying mechanism. The dose may be set in readiness when the conveying mechanism assumes the release position. The pre-defined dose metering positions may be only two different dose metering positions, so that two different product doses can be administered at different times of the day, for example. In other embodiments, more than two, e.g., a plurality of different dose metering positions are provided, to adapt to different situations and/or provide the option of enabling an individual dose to be set for product doses to be administered for a heterogeneous group of persons.

In accordance with some embodiments of the present invention, the dose metering mechanism is coupled to conveying mechanism by a blocking or lock engagement when the conveying mechanism assumes the triggering position. The blocking engagement may also exist already during the re-setting movement of the conveying mechanism. In the blocking engagement, the dose metering mechanism is locked against dose movements relative to the conveying mechanism in the previously set dose position. A forced movement out of the blocked dose position is only possible by applying an extraordinarily strong force and this results in the device being badly damaged, which then makes it impossible to use the device for administering the product any more. The advantage is that the dose is set in the release position and a "subsequent dose" can not then be set in the triggering position. Because it is blocked or locked in the triggering position, the injection device can be safely manipulated for administering purposes because the manipulations needed to proceed with the administering action can not accidentally lead to the set dose being adjusted. Although in some embodiments the dose metering mechanism is guided tightly in the blocking engagement to prevent movements transversely to the direction of the re-setting movement, a certain amount of clearance may be provided in principle, as long as there is no possibility of causing an adjustment to the set dose.

As mentioned above, the triggering position is a stop position. For dose metering purposes, this stop position is adjustable in and opposite the direction of the conveying movement and the maximum path length of the conveying movement is therefore also adjustable. The conveying mechanism and the dose metering mechanism respectively serve as a dose setting stop p and the two dose setting stops delimit the re-setting movement of the conveying mechanism and thus determine the triggering position. This means that one of the conveying mechanism and dose metering mechanism, in some preferred embodiments, the dose metering mechanism, forms a stop which can be varied in terms of its position. An example of an adjustable dose setting stop which differs from that of the present invention is disclosed in patent specification WO 97/36625. Based on the reverse kinematics in terms of their paths, i.e. as discrete dose setting stops, the dose setting stops disclosed therein could also be provided on the conveying mechanism, in which case it would be enough to provide a stop cam on the dose metering mechanism which is set in a dose position by the dose metering movement.

In some preferred embodiments, the dose metering mechanism is blocked due to the engagement of at least one selection element between two rotation stops. This ensures that, for each of the dose metering positions, one of the conveying mechanism and dose metering mechanism forms a selection element and the other forms two co-operating rotation stops which are locked with one another in engagement. As a result of the various different dose setting positions, several co-operating rotation stop pairs and/or several selection elements are provided, of which at least one pair is in the blocked engagement in each of the dose setting positions. In some preferred embodiments, several pairs are in a blocked engagement. The rotation stops or the selection element may be rigidly formed on the conveying mechanism and in particular may be integral with it. The at least one complementary element formed by the dose metering mechanism may be rigidly formed on the dose metering mechanism or may be integral with it.

The engagement between the selection element and the rotation stops may be released when the conveying mechanism is in the release position or may be provided in the form of a releasable catch engagement, which may advantageously also constitute at the same time the releasable catch engagement for the dose selection when the conveying mechanism is in the release position. In the latter variant, the blocking engagement becomes weaker during the movement into the release position up to of the catch engagement; conversely, the catch engagement prevailing in the release position becomes stronger relative to the blocking engagement during the re-setting movement of the conveying mechanism.

In some embodiments, the rotation stops may be provided in the form of guide grooves or projecting guide webs, which may extend over only a small part or over virtually the entire path length of the re-setting movement of the conveying mechanism. If the selection element is rigid, the rotation stops may extend as close as possible to the selection element when the conveying mechanism assumes the release position. In the release position, if the selection element or the several selection elements are in a releasable catch engagement with the guide or the rotation stops, the rotation stops extend accordingly across a longer distance.

In some preferred embodiments, the dose metering movement comprises a rotating movement of the dose metering mechanism relative to the conveying mechanism about a rotation axis. The dose metering movement may be a purely rotating movement. It may also be a super-imposed movement involving a rotating movement and a movement in translation, and, this being the case, along the rotation axis. The conveying movement of the conveying mechanism comprises a movement of the conveying mechanism relative to the dose metering mechanism along the rotation axis. In some embodiments, the conveying movement may be a purely linear movement along the rotation axis, and, in such embodiments, it may be that one of the structures, namely the conveying mechanism or the dose metering mechanism, at least partially surrounds the other about the rotation axis and the requisite number of rotation stops and/or selection elements are disposed on casing surfaces of the conveying mechanism and the dose metering mechanism lying opposite one another. The one of the two structures which at least partially surrounds the other, e.g., the dose metering mechanism, is or comprises a sleeve body and forms the rotation stops.

In some embodiments, the conveying mechanism may be made as a single part but also may be made up of several parts. In the case of the multi-part design, it comprises a conveying element which performs the conveying movement and thus acts directly on the product contained in the reservoir, and a drive mechanism which is coupled to the conveying element, causing its conveying movement. The drive mechanism comprises an output element and a drive element which can be moved relative to one another and are coupled to with one another so that a driving movement of the drive element causes an output movement of the output element. The output element may be rigidly connected to the conveying element or is coupled to the conveying element so that the output movement of the output element causes the conveying movement. The output element simply drives the conveying element with it during its output movement. The drive element is mounted so that it is able to perform the driving movement on the one hand and perform a movement opposite the direction of the driving movement into the triggering position of the conveying mechanism on the other hand. The drive element and the output element are coupled to one another so that the drive element drives the output element with it during the driving movement, whereas the driving element performs the movement in the opposite direction without the output element. Drive mechanisms of this type are known from injection pens, for example as disclosed in patent specifications WO 97/36625 and DE 199 00 792 C2. Also suitable would be a drive mechanism of the type described in patent specification DE 199 45 397 C2, for example, whereby the output element is smooth and the drive element has engaging elements which press into the smooth external surface of the output element. The movements of the conveying mechanism and, in the multi-part design, the movements of the elements of the conveying mechanism comprise or are linear movements along a translation axis of the conveying mechanism.

If, as in some preferred embodiments, the dose metering mechanism constitutes the rotation stops, its dose setting stop or dose setting stops, is or are disposed at the end of the rotation stops.

In some embodiments, the conveying mechanism is designed for manual activation. However, it may also have a motorised drive which causes the conveying movement and is triggered when the conveying mechanism is in the triggering position. In both embodiments, it has an operating element, in the one instance for manual activation and causing the conveying movement and in the other instance for triggering the motorised drive. In the case of manual activation, which may be preferred for applications involving injection devices, the user applies the force needed to produce the conveying movement by means of the operating element.

Advantageously, a path length which the operating element travels during activation is larger or longer than a path length of the conveying movement which the conveying mechanism travels in order to dispense completely the set product dose. This larger path length is of particular advantage if the path length of the conveying movement corresponding to the set product dose is very short, for example one or a few millimeters or even less than one millimeter. If the movement of the operating element likewise extended over such a short path length, misinterpretations could arise and the user might think that he had not administered the product dose or had not completely administered it.

The longer activation path of the operating element compared with the conveying movement can be achieved on the basis of a gear mechanism whereby the movement of the operating element is constantly and continuously reduced in the conveying direction by means of a reducing gear. Not least for reasons of simplicity, however, the activation path of the operating element comprises a free movement of the operating element without any conveying movement and a joint movement of the operating element with the conveying movement 1:1.

In another embodiment, the drive and dose metering module has a dose metering element which can be moved relative to a drive member into one of several dose setting positions to set or select the product dose (i.e., the amount to be delivered), wherein one of the drive member and dose metering element forms several dose stops at different axial heights and rotation stops assigned to the dose setting stops, and the other of the drive element and dose metering element forms at least one selection element. The drive member can be moved in translation relative to the dose metering element as far as a triggering position in which the at least one selection element is in abutment with one of the dose setting stops. In the triggering position, the at least one selection element with the rotation stops locks the rotation of the dose metering element in both directions.

In some embodiments, the dose metering element corresponds to a dose setting mechanism. The dose metering element may specifically be sleeve-shaped and can be rotated relative to the drive element in order to set the product dose. Depending on the rotation angular position, several dose setting positions can be set as a result. The dose metering element may have several dose setting stops, which may be distributed on the external peripheral surface and, if the dose metering element is sleeve-shaped, on the internal circumferential surface of the sleeve. The dose setting stops sit at different positions in the axial direction so that the drive member can be moved along paths of differing lengths in the axial direction, depending on the set dose. In some preferred embodiments, the dose metering element can be rotated relative to the output element into one of several dose setting positions in order to set the product dose, in which case the drive element is mechanically coupled to the output element and can be moved in translation relative to the output element. The product dose advantageously depends on the different axial heights of the several dose setting stops. The dose setting stops may be distributed around the periphery.

The dose setting stops may respectively be provided in the form of an end face of a groove, in which case the groove extends axially from a front face of the component containing the dose setting stops into the component. The groove is advantageously open across a half side in its longitudinal direction so that the selection element is able to slip into the groove or be moved into it. The grooves may be provided on an inner circumferential surface of a sleeve or on an external face of an element locating in a sleeve. In one preferred embodiment, the grooves extend in the axial direction and have a pocket-type shape so that the selection element is only able to engage in the groove from the internal face. The depth of the pocket-shaped grooves is shorter than the wall thickness of the sleeve. In principle, the grooves could be of a continuous design so that their depth corresponds to the wall thickness of the sleeve. Starting from the end face or at an axial distance from the end face of the component containing the dose setting stops, the grooves may extend as far as the dose setting stops.

In some embodiments, webs serving as rotation stops remain between the grooves which are advantageously disposed around the circumference. In particular, the rotation stops are formed by the sides of the groove or grooves.

In one preferred embodiment, one of the drive element and dose metering element has dose setting stops axially directed towards the other in a stepped arrangement. Here too, the sides of the grooves may form the rotation stops. A rotation stop should be disposed between each stage of the stepped arrangement. In principle, it is also possible to dispense with a web between some stages. The groove may also form two or more dose setting stops at its end face. The dose setting stops disposed in a stepped arrangement in the circumferential direction may be of a constantly rising and constantly descending design but this is not intended to imply that they are restricted to these options. In one preferred embodiment, the dose setting stops are formed by the dose setting element and the at least one selection element is formed by the output element. The at least one selection element may be a cam or a web extending in the axial direction, which preferably projects out from a casing surface of the drive element or the dose setting element. Three selection elements may be provided.

In some embodiments, a mechanism holder may be provided, with which the dose setting element is mechanically coupled, in which case the dose setting element may be rotated relative to the mechanism holder. The drive element may also be mechanically coupled to the mechanism holder, in which case the drive element can be moved in translation relative to the mechanism holder.

In another embodiment, the drive and dose setting module has a dose setting element and a mechanism holder, relative to which the dose setting element can be rotated, and one of the mechanism holder and dose setting element has at least one locking element and the other of the mechanism holder and dose setting element has at least one lock complementary element, in which the lock element can engage and lock to prevent rotation of the dose setting element relative to the mechanism holder. The lock element may be resilient in the radial direction. The resilient arrangement may be achieved by means of a spring element. The spring element may be a spring for example. The spring may be formed by a portion of the component incorporating the lock element. In some preferred embodiments, the at least one lock element, the at least one spring element co-operating respectively with the at least one lock element and one of the mechanism holder and dose setting element are integral, and in some embodiments, the at least one lock element is formed on the dose setting element, in which case the at least one lock complementary element is formed on the mechanism holder.

The number of lock complementary elements may be greater than or the same as the number of lock elements. In some embodiments, the number of lock complementary elements corresponds to the number or a multiple of the number of dose setting stops. The number of lock complementary elements may also be only a fraction of the number of dose setting stops. In principle, the lock complementary elements are distributed in the circumferential direction. It may also be of advantage if the lock complementary elements are disposed in certain portions around the circumference. One of the dose setting element and the drive element advantageously has several dose setting stops distributed about the circumference, in which case several lock complementary elements are provided with the same angular pitch as the dose setting stops. The at least one locking element should be disposed in a positional relationship with the dose setting stops and/or the grooves co-operating with them such that at least one locking element is able to slip respectively into a lock complementary element when the at least one selection element is moved into a groove of the component containing the dose setting stops. The angular pitch of the dose setting stops and hence also that of the lock complementary elements may be identical. However, a different angular pitch would also be conceivable.

In some preferred embodiments, a blocking element may hold the lock element in a locking engagement with the lock complementary element. This locks the rotation of the dose setting element relative to the mechanism holder. In one embodiment, the lock element may be disengaged from the lock complementary elements and engaged with the lock complementary element by the blocking element so that the rotation of the dose setting element relative to the mechanism holder is locked. In another embodiment, the lock element is engaged with the lock complementary element without the blocking element holding the lock element in the locking engagement. When the dose setting element rotates, the lock element is pushed out of the lock complementary element and as the rotation continues, latches in the next or adjacent lock complementary element. This is continued until the desired dose has been set by rotating the dose setting element. Since the lock element is blocked by the blocking element, the lock element can no longer slip out of the lock complementary element, as a result of which the rotation of the dose setting element relative to the mechanism holder is locked. The blocking element is moved in translation into a blocking engagement with the lock element. It would also be conceivable for the blocking engagement to be obtained by a rotating movement or a combination of a rotating movement and a movement in translation.

In some embodiments, a blocking element is formed on or by an operating element. The blocking element may be provided in the form of a radially projecting circumferential collar or a shoulder of a sleeve, and should release the lock element at least in a release position. The lock element or elements is or are blocked as long as the blocking element is lying opposite them. The blocking element may extend in the longitudinal direction across a length which is large enough to prevent rotation across a long extraction path of the operating element. It would also be conceivable for the blocking element to be only so long that it prevents rotation at the smallest possible dose or the first smallest possible doses. The blocking element could block the lock element if, when there are one or more selection elements, not all the selection elements are engaged with the grooves. An axial length of the blocking element may be shorter than the path by which the blocking element can be moved in translation for a maximum set dose minus twice the axial length of the lock element. This being the case, the blocking element would release the lock element at a high dose but at the latest by the maximum possible dose. The blocking element could also then release the lock element if, when there are one or more selection elements, all the selection elements engage with a groove. Rotation would then be blocked by means of all the selection elements moved into the groove or into the grooves. This would enable the structural length of the drive and dose metering module to be reduced.

In another embodiment, the at least one selection element may be of a multi-part design. It would be conceivable to provide two or more selection part-elements axially one after the other. At least one of the selection part-elements may be moved into abutment with a dose setting stop in order to select the dose. Another of the selection part-elements may be used as an anti-rotation lock.

In another embodiment, at least one groove constituting the rotation stops is spaced apart from the dose setting stop. In principle, the groove or the webs forming the sides of the groove could be interrupted in their axial extension. The webs may act as an axial guide. A selection part-element forms an anti-rotation lock, for example in conjunction with the sides of the groove, in which case the other selection part-element is moved into an axial abutment with the dose setting stop to select the dose.

In some embodiments, the drive and dose setting module may be fitted with the different mechanisms described above, which prevent a product dose from being metered outside the release position. Features of the present invention may be used in any combination with one another.

DETAILED DESCRIPTION

Figure 1:
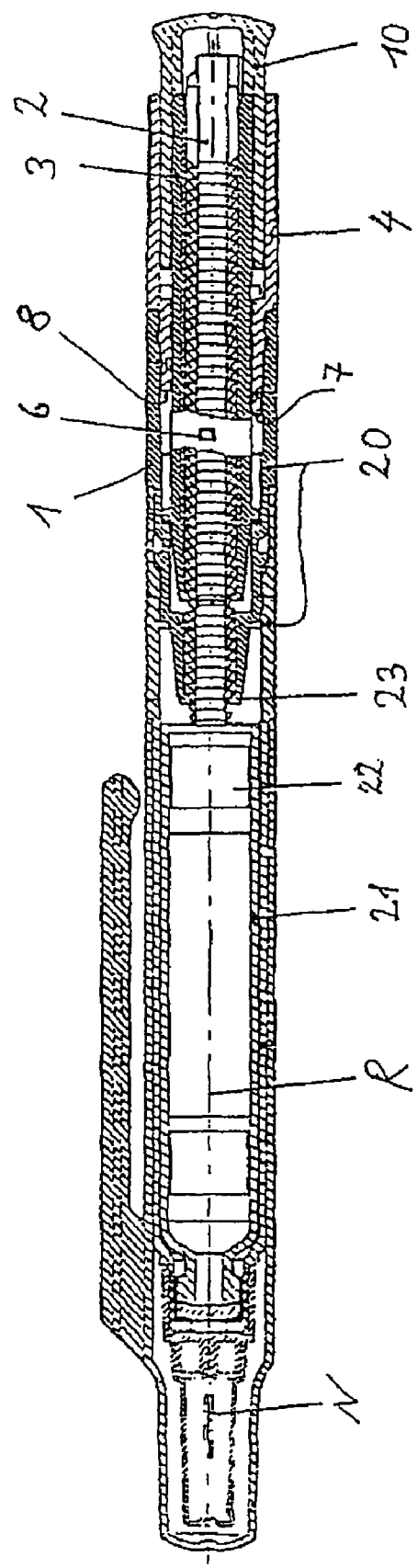
FIG. 1 illustrates an embodiment of an injection device.

FIG. 1 shows an embodiment of an injection device in the form of an injection pen in accordance with the present invention. The injection device has a two-part housing 20 comprising a distal (or front or forward) housing portion and a proximal (or back or rear) housing portion, which are fixedly connected to one another, for example screwed together. A housing compartment of the housing 20 forming its distal housing portion contains a reservoir 21. Attached to a distal outlet of the reservoir 21 is an injection needle N. The longitudinal axis of the injection needle N forms a central longitudinal axis R of the injection device. A plunger 22 closes off the proximal end of the reservoir 21. The plunger 22 is able to perform a conveying movement along the axis R onto the outlet of the reservoir 21 in order to force product out of the reservoir 21. The reservoir 21 is a commercially available ampoule, filled with the product to be administered, for example insulin.

The plunger 22 is the conveying element of a conveying mechanism acting directly on the product, which, in addition to the plunger 22, also has an output element 2, a drive element 3 and an operating element 10. Due to the fact that the conveying element is provided in the form of a plunger 22, the output element 2 acting directly on the plunger 22 is a plunger rod and will therefore be referred to as such herein. When the conveying mechanism is activated, the plunger rod 2 also performs the conveying movement and thus forces the plunger 22 in the distal direction. The plunger rod 2 is provided in the form of a toothed rack with several rows of teeth extending in the direction of the axis R which are respectively offset from one another along the axis R by less than one tooth pitch in order to make the dose selection finer. The drive element 3 can be moved along the axis R in the distal and proximal direction. The drive element 3 and the plunger rod 2 are coupled to one another so that the drive element 3 drives the plunger rod 2 with it as it moves in the distal direction but performs the movement in the proximal direction without the plunger rod 2. In the embodiment illustrated as an example, the coupling is brought about by the engagement of drivers in the rows of teeth of the plunger rod 2. The engagement is such that a movement of the plunger rod 2 in the distal direction relative to the drive element 3 is prevented and a movement of the drive element 3 in the proximal direction relative to the plunger rod 2 is permitted. To prevent the plunger rod 2 from being driven during the movement in the proximal direction, the proximal portion of the housing 20 forms a retaining mechanism 23 which, like the driver of the drive element 3, engages in at least one, but in the embodiment illustrated as an example, two rows of teeth of the plunger rod 2 so that the plunger rod 2 can be moved relative to the housing 20 in the distal direction but not in the proximal direction. This is achieved due to the fact that the teeth of the rows of teeth are of a saw-tooth shape. The proximal portion of the housing 20 provides a mount for the plunger rod 2 as well as the drive element 3 so that these elements of the conveying mechanism are not able to perform any rotating movements about the axis R relative to the housing 20. Since the proximal portion of the housing 20 at least partially incorporates the dose metering and administering mechanism, it may also be termed a mechanism holder 1.

For every injection, the injection device enables the free selection of a product dose which can be administered. To select and/or set the product dose, a dose metering element 4 is provided, which is able to perform a dose metering movement relative to the conveying mechanism, in particular relative to its drive element 3. The proximal portion of the housing 20 also accommodates the dose metering element in an appropriate manner for performing the dose metering movement. In the embodiment illustrated as an example, in which the dose metering movement is a rotating movement about the axis R, the mechanism holder 1 of the housing 20 provides a mount for the dose metering mechanism 4 enabling it to rotate about the axis R. The axis R therefore forms the translation axis for the conveying mechanism and the rotation axis for the dose metering element 4. When performing the dose metering movement, the dose metering element 4 can be moved between discrete pre-defined dose setting positions in the form of catch positions. To this end, it sits in a releasable catch engagement with the proximal portion of the housing 20 in each of the dose setting positions. As regards the dose metering element 4, it should also be pointed out that in the embodiment illustrated as an example, it is provided in the form of a sleeve body and surrounds the drive element 3 as well as the operating element 10. The drive element 3 and the operating element 10 are likewise each provided in the form of a sleeve body, whereby the operating element 10 surrounds a proximal end portion of the drive element 3 and projects out of the dose metering element 4 in the proximal direction to permit manual activation of the conveying mechanism. The drive element 3, finally, surrounds the plunger rod 2.

To set the product dose, the drive element 3 constitutes a selection element 6 and the dose metering element 4 a dose stop 8 lying opposite the selection element 6 in the proximal direction. The dose setting element 4 forms its dose stop 8 by means of a distal end face, which respectively bounds two rotation stops 5 extending from the distal end face 7 of the dose metering element 4. The drive element 3 forms its selection element 6 by means of a cam projecting radially outwards, the shape of which is adapted to the width of a groove 9 formed by two rotation stops or to the width of the dose stop 8, respectively.

In the state illustrated in FIG. 1, the conveying mechanism has assumed a position in the housing 20 closest to the distal end. In this state, the product dose is set by means of the dose metering element 4, whereby a dose setting stop 8 corresponding to the desired product dose is moved along the axis R into the dose metering position lying opposite the selection element 6. The distance left between the dose setting stop 8 and selection element 6 and 27 as measured along the axis R in the relevant dose metering position corresponds to the path length, i.e. the conveying stroke, which the drive element 3 can cover together with the plunger rod 2 and the plunger 22 during the injection. After setting the product dose, the drive element 3 and, due to the engagement, the plunger rod 2 with it are pulled in the proximal direction by pulling on the operating element 10 until the selection element 6 makes contact with the dose setting stop 8. The conveying mechanism then assumes a triggering position, from which a pressing force acting on the operating element 10 can be applied in the distal direction for the injection. It is clear that prior to the injection, the housing cap illustrated in FIG. 1 as well as the needle guard cap must be removed.

The proximal portion of the housing 20, the parts of the conveying mechanism mounted by this portion and the dose metering element 4 fixedly connected to the housing portion except for the dose metering movement constitute a drive and dose metering module, may be of the type known from patent specification DE 199 00 792 C2. This module may be replaced by a drive and dose metering module of the type provided in accordance with the present invention.

Figure 2:
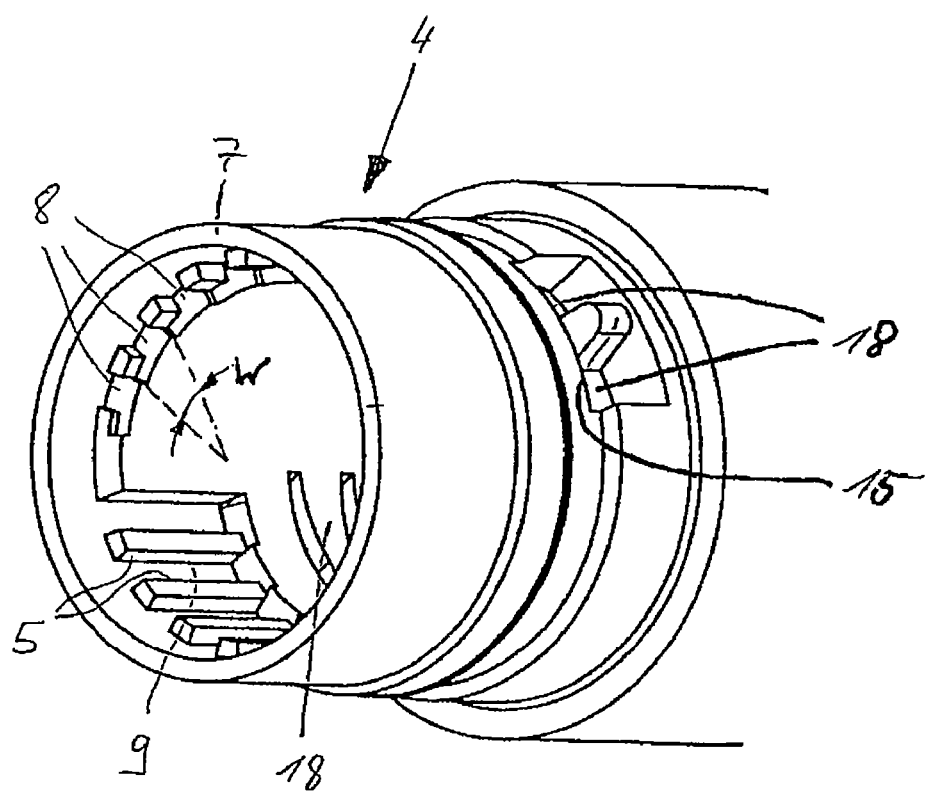
FIG. 2 is a perspective view of an embodiment of a dose metering mechanism in accordance with the present invention.

FIG. 2 illustrates an exemplary embodiment of a drive and dose metering module in accordance with the present invention. Parts which fulfill the same functions as those of the drive and dose metering module shown in FIG. 1 are denoted by the same reference numbers.

The drive and dose metering module of the present invention has a dose metering lock in the form of several rotation stops 5, which prevent the set product dose from being adjusted when the conveying mechanism is in the triggering position. The dose metering lock is based on an engagement between the conveying mechanism and the dose metering element 4, which blocks dose metering movements of the dose metering element 4 relative to the conveying mechanism when the conveying mechanism is in the triggering position and will therefore be referred to as a blocking (or locking) engagement.

FIG. 2 illustrates a dose setting mechanism 4 in the form of a dose metering element 4. The dose metering element 4 is of a sleeve-shaped design. The external face of the sleeve has several shoulders, which, amongst other things, serve as a gripping surface or element by which a coupling with a mechanism holder 1 is possible. Disposed on the internal face of the sleeve are dose setting stops 8. The dose setting stops 8 are disposed at different axial heights. In particular, the dose setting stops 8 are distributed around the circumference in a stepped arrangement. In the example illustrated, the step descends constantly and rises constantly. The angle between one dose setting stop 8 and the next dose setting stop 8 or any other dose setting stop 8 is shown by W denoting the angular pitch. The angular pitch W and/or the number of dose setting stops 8 should correspond to that of the lock complementary elements 16 in the mechanism holder 1, for example.

Between the step stages or the dose setting stops, webs extend in the longitudinal direction, which form rotation stops by means of their sides. The combination of two webs and at least one dose setting stop 8 may also be described as a groove 9, in which case the groove 9 is open at one half face and the sides of the groove 9 form the rotation stops 5. The webs contained by the rotation stops 5 project respectively from a dose setting stop 8 in the longitudinal direction R, the height and width of the web being shorter than the height and width of the co-operating dose setting stop. Using this design of web incorporating the dose setting stop, an end face 19 (FIG. 3) of a selection element 6 may be made in a stronger and more wear-resistant design. The distance between two sides 5 forming a groove 9 is bigger than the width B of a selection element 6.

The end faces of a web, formed on the open end face of a groove 9, are axially offset into the dose metering element 4 from an end face 7 of the dose metering element 4.

Figure 10:
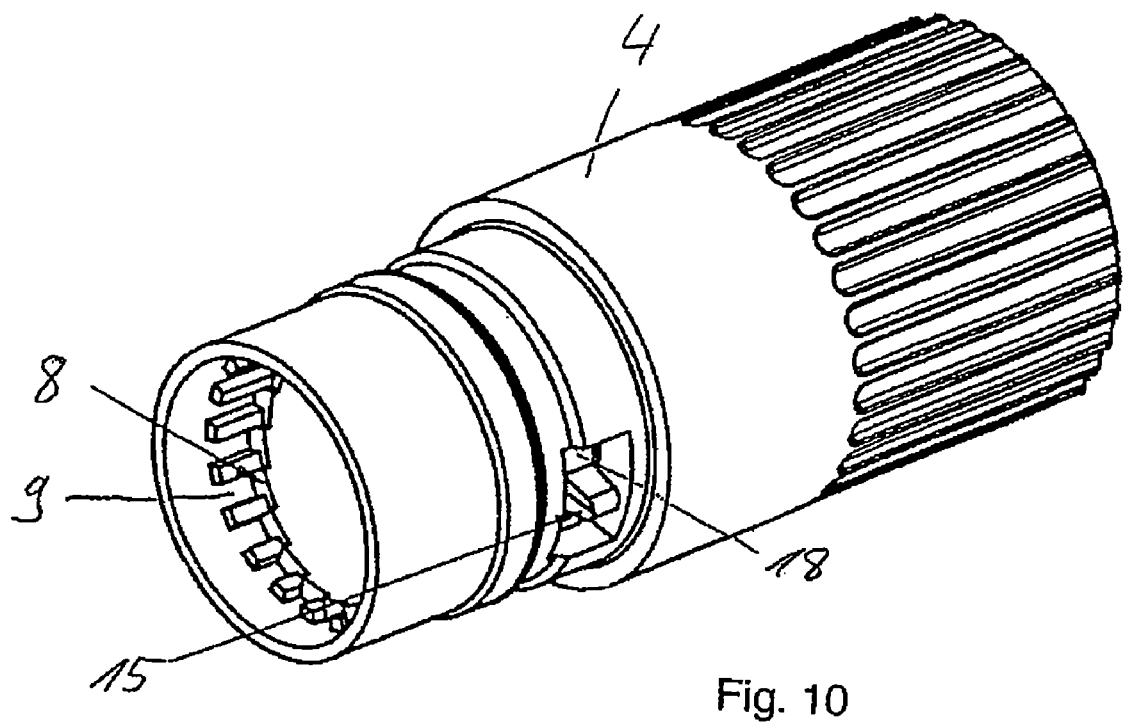
FIG. 10 is a perspective view of an embodiment of a dose metering mechanism.
Figure 11:
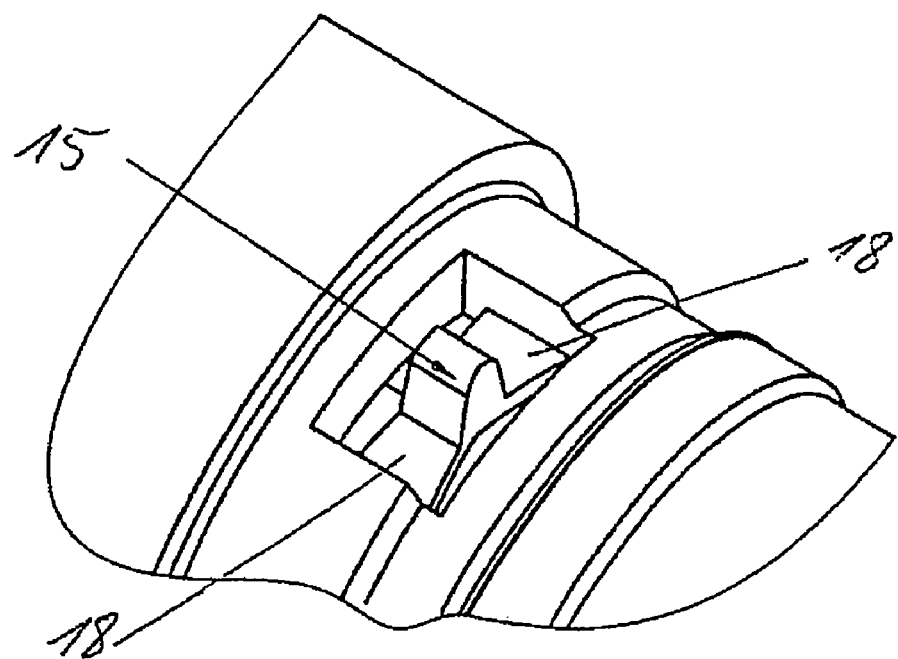
FIG. 11 shows an embodiment of a lock element in accordance with the present invention.

FIGS. 2, 10 and 11 specifically illustrate two locking elements 15, lying diametrically opposite one another, which are disposed on the dose metering element 4 so that they are resilient in the radial direction. The locking element 15 is disposed in a window-type orifice of the dose metering element 4. The dose metering element 4 forms two spring elements 18, each of which is connected to the lock element 15. Due to the structural design of the spring elements 18, the lock element 15 is able to spring in the radial direction. In the example illustrated, the lock elements 15, spring elements 18 and dose metering element 4 are made in a single piece. The lock element 15 is rounded at its end pointing radially outwards, to enable it to latch more easily out of and into the next or adjacent lock complementary element 16. Due to the dose setting movement of the dose metering element 4, the lock element 15 is forced out of the respective lock complementary element 16 due to its advantageous design and latches in the next lock complementary element 16 as a result of the spring action of the spring elements 18.

Figure 3:
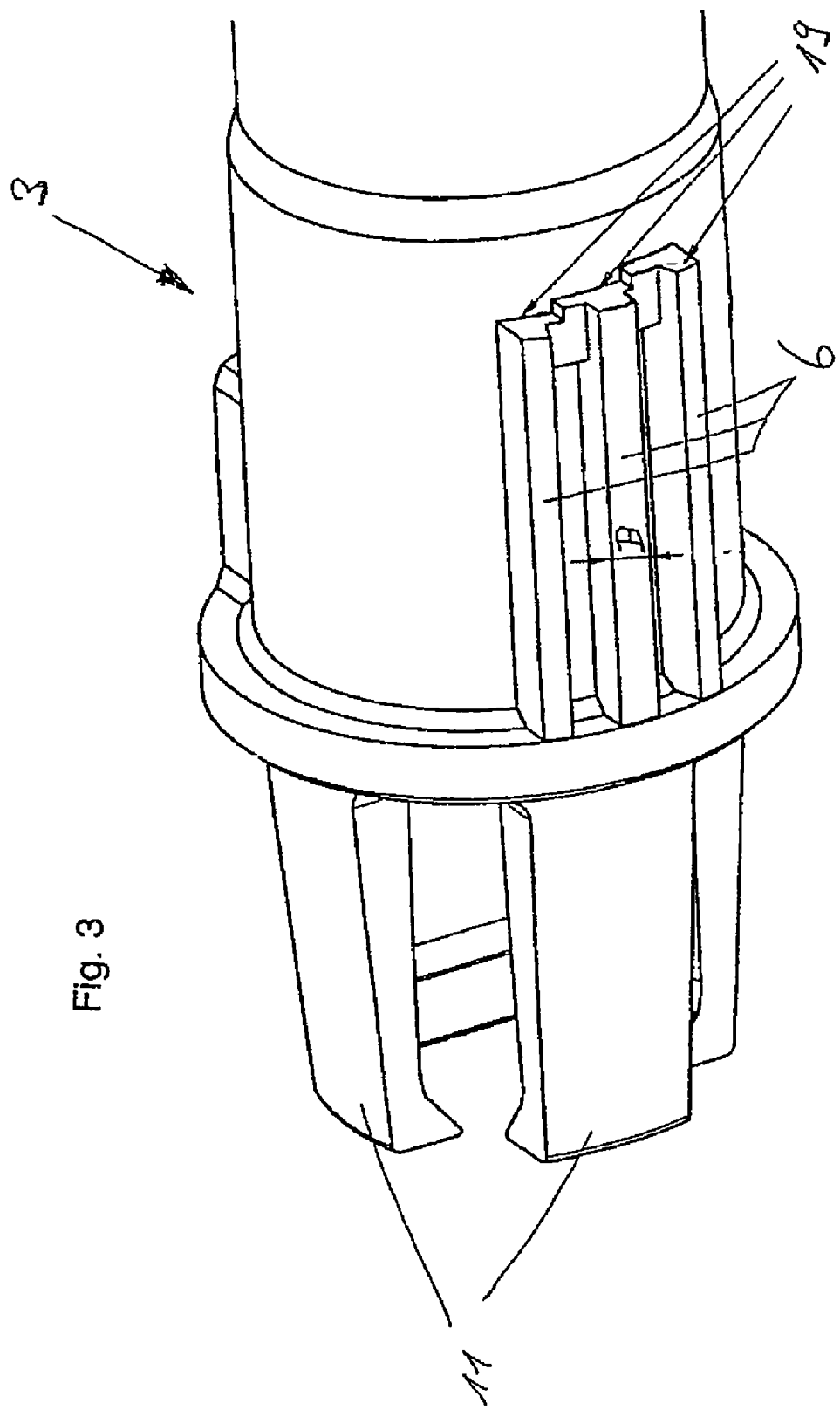
FIG. 3 is a perspective view of an embodiment of a drive element in accordance with the present invention.
Figure 9:
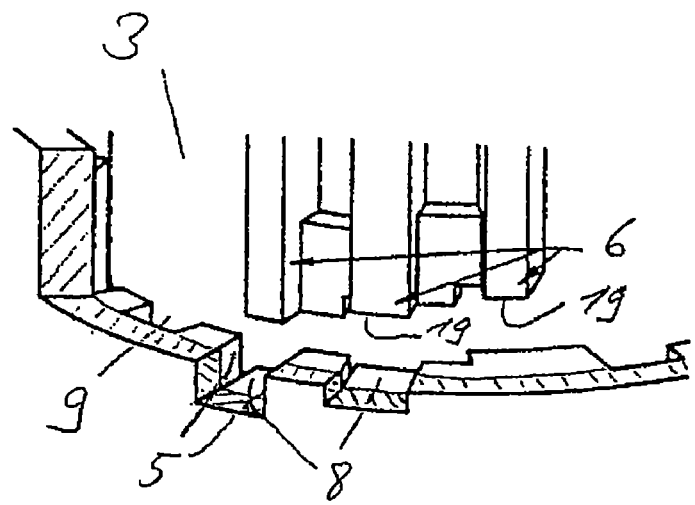

FIGS. 3 and 9 illustrate a drive element 3 in accordance with the present invention. At its distal end, the drive element 3 has several retaining mechanisms 11 for an output element 2. In particular, at least one selection element 6 is disposed on the outer peripheral surface of the drive element 3. As may be seen from FIG. 3, it is of particular advantage to provide three selection elements 6 on the drive element. The shape of the end faces 19 of the selection elements 6 more or less matches the mirror image of the dose setting stops 8. In the example illustrated, the selection elements 6 are webs extending in the longitudinal direction R, the width B of which is adapted so that they can be moved into the grooves 9 of the dose metering element 4.

Figure 4:
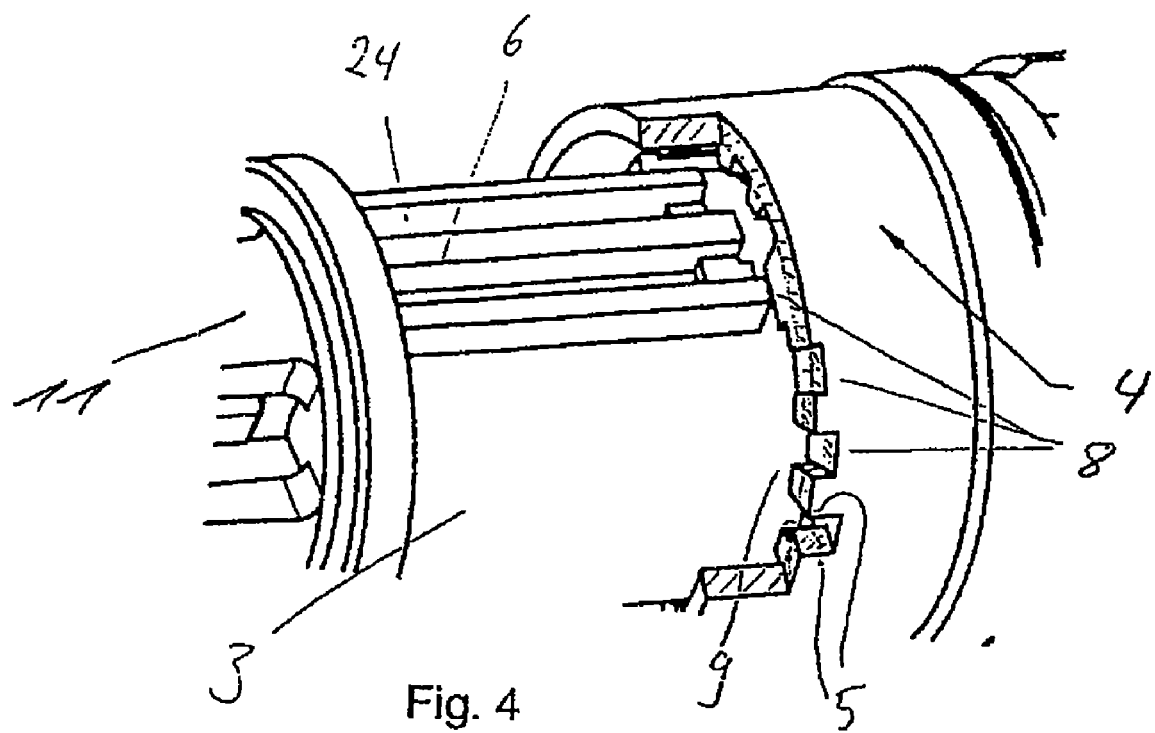
FIGS. 4-9 illustrate how the dose metering mechanism and drive element co-operate in accordance with the present invention.

FIG. 4 illustrates the drive element 3 and the dose metering element 4 in a release position. The dose metering element 4 can be rotated relative to the drive element 3. None of the three selection elements 6 is engaging in a groove 9 of the dose metering element 4.

Figure 5:
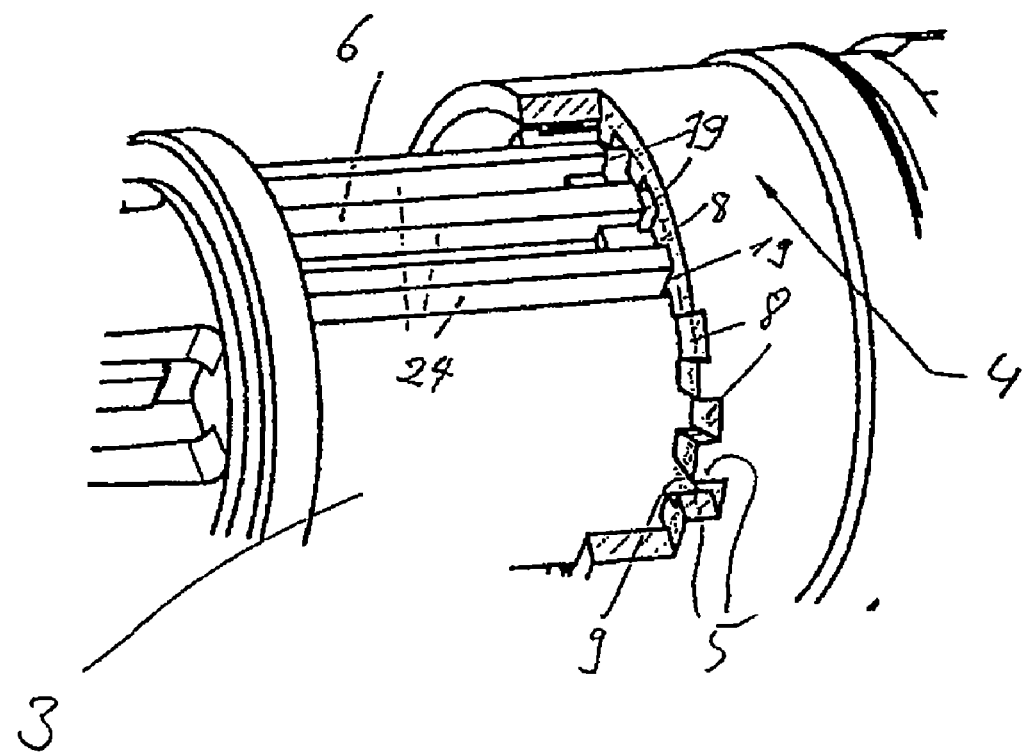

FIG. 5 illustrates the dose metering element 4 and the drive element 3 in a triggering position for at least a smallest possible product dose. The end faces 19 of the selection elements 6 are also disposed at different axial heights matching the dose setting stops 8. Consequently, only one end face 19 is in abutment with a dose setting stop 8. This example does not enable rotating movement to be locked because the selection element 6 does not engage in a groove 9. To prevent the dose metering element 4 from nonetheless twisting against the drive element 3, it is advantageous to additionally secure the dose metering element 4 against rotation using a lock element 15.

Figure 6:
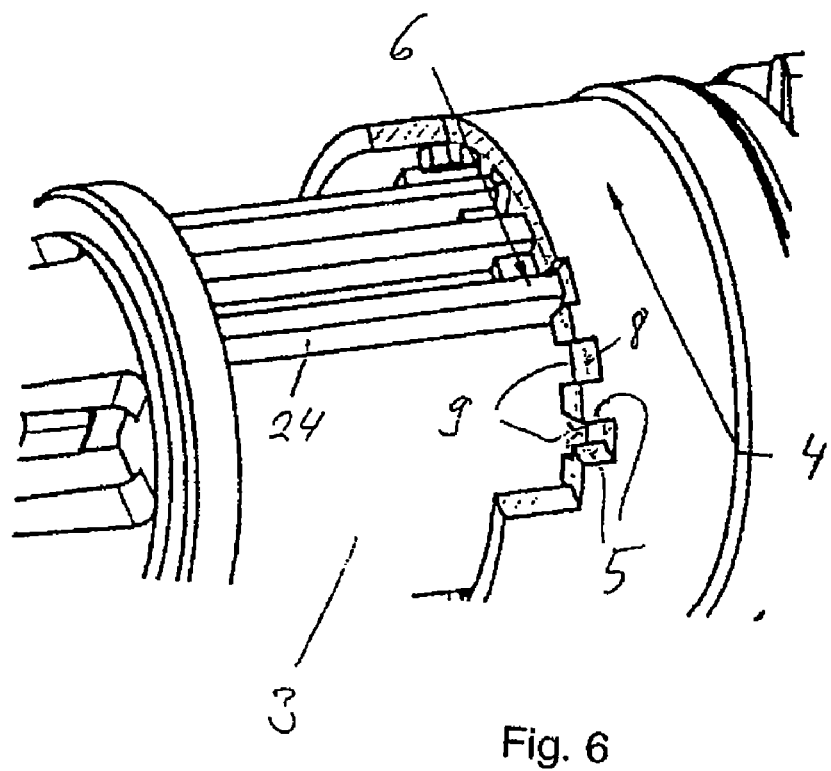

FIG. 6 illustrates the dose metering element 4 and the drive element 3 in a triggering position, in which an end face 19 of two selection elements 6 respectively sits in abutment with a respective dose setting stop 8. In addition, one selection element 6 is engaged in a groove 9 by means of its sides 24, as a result of which the dose metering element 4 is prevented from rotating against the drive element 3 in both directions. The overlap of the sides 24 of the selection element 6 with the rotation stops 5 is only very slight, however, so that a slightly higher torque on the dose metering element 4 could possibly lead to twisting of the dose metering element 4 against the drive element 3. The dose metering element 4 is therefore additionally prevented from rotating by means of one, preferably two, lock elements 15.

Figure 7:
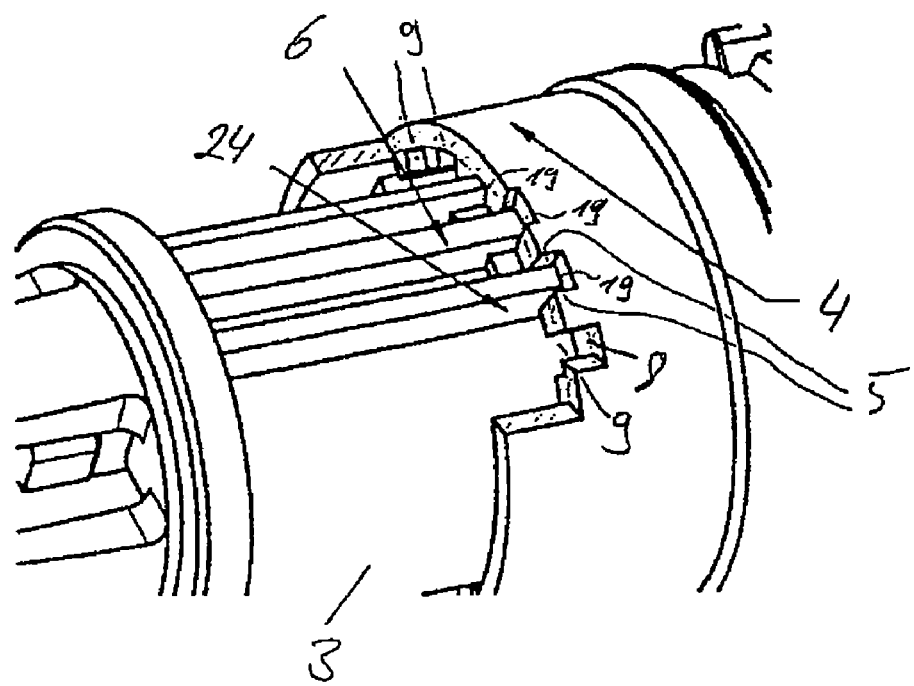

FIG. 7 illustrates the end faces 19 of the selection elements 6 respectively in abutment with a dose setting stop 8. Two of the three selection elements 6 have latched into the grooves 9 and form an anti-rotation lock. The overlap of the sides 24 with the rotation stops 5 is somewhat bigger than was the case with FIG. 6. It would also be of practical advantage to provide additional anti-rotation locking by means of lock elements 15.

Figure 8:
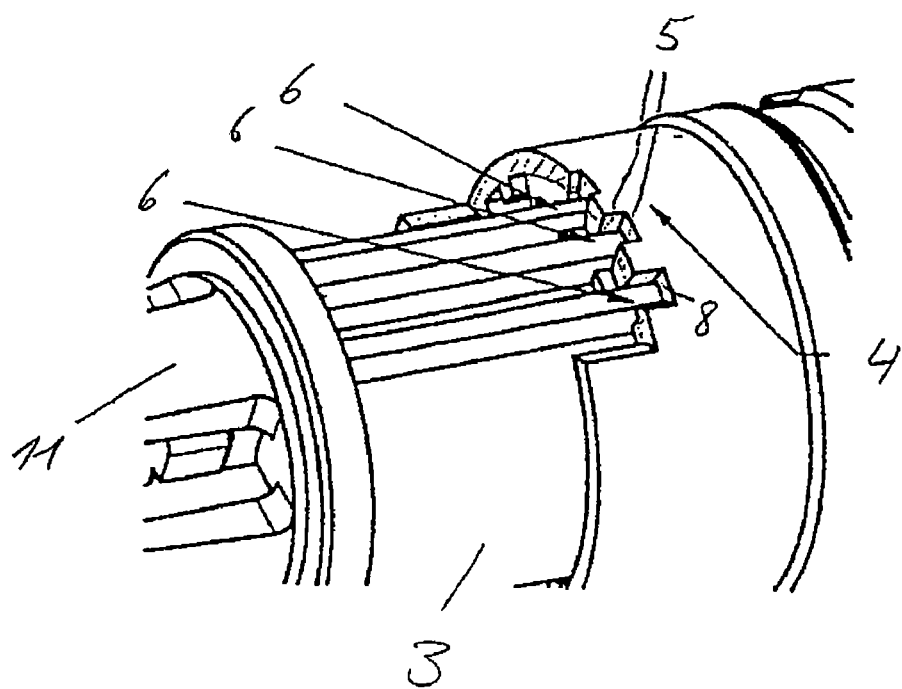

In FIG. 8, the drive element 3 is in a triggering position, in which case all three selection elements 6 have latched into a groove 9, thereby providing an anti-rotation lock in both directions. In principle, the tightness of the locking action of the dose metering element 4 against the drive element 3 also increases with the set product dose. Consequently, in the case of a higher product dose, the additional anti-rotation lock provided by the lock elements 15 can be dispensed with. The lock elements 15 prevent the dose metering element 4 from rotating against the drive element 3 only as long as all engaging elements locate respectively in a groove for the first time.

FIGS. 12-15 illustrate the drive and dose metering module used in one embodiment of the present invention. It comprises a mechanism holder 1, which might also be termed a proximal housing portion 1. At its front end, the mechanism holder 1 forms retaining mechanisms 23 which are attached to the distal end of the mechanism holder 1 in an oscillating manner so that they are able to bend elastically about their anchoring point. The retaining mechanism 23 engages in an output element 2. The output element is a forward-drive rod or a rod with teeth of a saw-tooth design. The retaining mechanism 23 and plunger rod 2 engage with one another due to their saw-tooth contours. The oblique surfaces of the teeth point in the distal direction, in other words, in the direction in which the plunger of the reservoir will subsequently be moved.

The mechanism holder 1 partially encloses a dose metering element 4 and simultaneously provides a mount for it. The dose metering element 4 is mounted in the mechanism holder 1 so that it is only able to move in rotation. This is achieved due to the fact that catch lugs are provided on the mechanism holder 1, which locate in a radial groove extending around the dose metering element 4, thereby preventing axial movement of the dose metering element 4 relative to the mechanism holder 1. The dose metering element 4 may have several shoulder-type peripheral surfaces. Disposed at the proximal end of the dose metering element 4 is a portion which forms a surface enabling a user to rotate the dose metering element 4 relative to the mechanism holder 1. This surface may be referred to as a gripping surface 14. Formed on another portion of the dose metering element 4 is a scale drum 12, on the peripheral face of which is a scale from which a user of the device can take a reading of the product dose he has set. To this end, the mechanism holder 1 has a window, enabling one of the scale values to be read from the scale 13.

The dose metering element 4 may correspond to the dose metering elements 4 already described. The dose setting stops 8 are at different axial distances from the end face 7. These different distances of the dose setting stops 8 from the end face 7 each correspond to a product dose. The number of grooves 9 may determine the number of individual elements of the scale 13. Preferably, the number and pitch of the elements of the scale 13 are the same as that of the stepped arrangement of the dose setting stops 8.

The dose metering element 4 provides a mount for the drive element 3. A relative rotating movement is possible between the drive element 3 and dose metering element 4. The drive element 3 is also mounted by means of the mechanism holder 1. The drive element 3 is able to perform translating movements only relative to the mechanism holder 1. This is due to mutually engaging elements formed between the mechanism holder 1 and the drive element 3. In some preferred embodiments, the mechanism holder 1 is provided with a cam or some other projecting structure, which engages in a groove in the mechanism holder 1. The groove is oriented in the axial direction. This prevents the rotating movement of the drive element 3 relative to the mechanism holder 1 but permits the axial movement.

Disposed at the distal end of the drive element 3 are retaining mechanisms 11 which, like the toothed rack 2, have teeth of a saw-tooth design and engage in the plunger rod 2. The retaining elements 11 are formed as wings and are attached to the distal end face of the drive element 3. The retaining mechanisms 11 are able to move elastically backwards and forwards about their anchoring point on the drive element 3. The retaining mechanisms 11 of the drive element 3 correspond to those of the retaining mechanisms 23 of the mechanism holder 1.

At its proximal end, the drive element 3 has a connecting element, which enables a connection with an operating element 10. The operating element 10 and drive element 3 are connected to one another in such a way that when the operating element 10 is pulled out of the dose metering element 4, the drive element 3 is driven with it.

The drive element 3 may correspond to the drive elements 3 already described. The dimensions of the selection element 6 are such that the selection element 6 can be moved into the grooves 9.

As described above, the lock elements 15 are disposed so that they spring in the radial direction and may be an integral part of the dose metering element 4. Several lock complementary elements 16 are uniformly distributed around the mechanism holder 1, e.g., in the circumferential direction. Since a single lock element 15 would be sufficient to provide an anti-rotation lock in principle, the way in which the one lock element operates will be described, although the explanation also applies if several lock elements 15 are provided. In the release position, the dose metering element 4 is able to rotate against the mechanism holder 1. In the embodiments illustrated in FIGS. 12-15, the lock element 15 is in the release position, in a latched engagement with a lock complementary element 16. The lock complementary elements are catch grooves, for example, lying opposite the lock element 15. By rotating the dose metering element 4, the lock element 15 is forced radially inwards and out of the respective lock complementary element 16 due to the rotating movement. The lock complementary element 16 latches into the next lock complementary element 15. A blocking element 17 is designed so that it is able to block the inwardly directed movement of the lock element 15. The blocking element 17 is a collar on the operating element 10 pointing radially outwards. In order to block the latching movement of the lock element 15, the operating element 10 is moved in the proximal direction so that the blocking element 17 is moved in a region within the lock element 15 and thus blocks the latching movement of the lock element 15. As an alternative, the lock element 15 could also be disengaged from out of the lock complementary element 16 in the release position. Due to the blocking element 17, the lock element 15 could be engaged with one of the lock complementary elements 16. Due to the movement of the operating element 10 in the proximal direction, the blocking element 17 would push the lock element 15 radially outwards so that the lock element 15 in conjunction with the lock complementary element 16 would ensure that any rotation was prevented in both directions.

To set a dose, the grooves 9 are turned by rotating the dose metering sleeve 4 relative to the drive element 3 until the desired grooves 9 lie opposite the selection elements 6. The dose is determined on the basis of the axial distance between the dose setting stops 8 and the selection elements 6. The product dose is set by means of the different depths of the grooves 9 and due to the axial height of the dose setting stops 8. When the desired grooves 9 lie opposite the selection elements 6, the operating element 10 is pulled out relative to the dose metering sleeve 4 so that the selection elements 6 move into the desired grooves 9 as far as the dose setting stops 8. The rotation stops 5 prevent any adjustment being made to the dose by means of the dose metering sleeve 4. By extracting the operating element 10 and the drive element 3 coupled to it, the retaining mechanisms 11 perform an outward swinging movement because their surfaces extending at an angle to the longitudinal axis slide on one another. In the release position, the retaining mechanisms latch into the plunger rod 2. The plunger rod 2 is not pulled back by the backward movement of the operating element 10 because the retaining mechanisms 23 prevent the plunger rod 2 from being pulled back.

To administer the product, the operating element 10 is pushed in the distal direction so that the drive element 3 coupled to it also moves the retaining mechanisms 11 in the distal direction. Due to the teeth of the retaining mechanism 11, the output element 2 is also driven along in the distal direction. The retaining mechanisms 23 of the mechanism holder 1 therefore snap out and only then snap back in again once the movement of the plunger rod 2 has ended, due to the oblique surfaces of the teeth.

Figure 12:
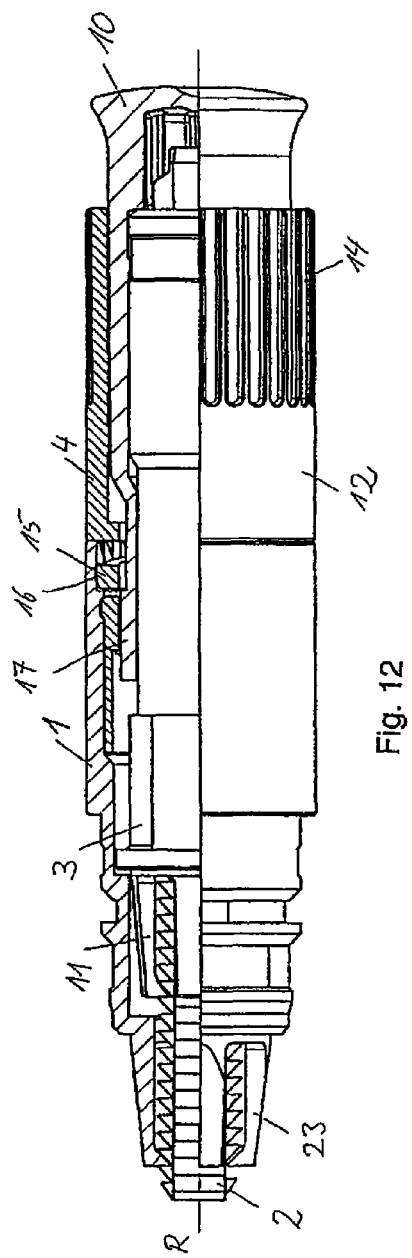
FIGS. 12-15 illustrate an embodiment of a drive and dose metering module in accordance with the present invention.

FIG. 12 illustrates the drive and dose metering module in a release position prior to administering. The blocking element 17 is not in the region of the lock element 15 and the lock element 15 is therefore able to perform inwardly directed latching movements. The dose is set by rotating the dose metering element 4.

Figure 13:
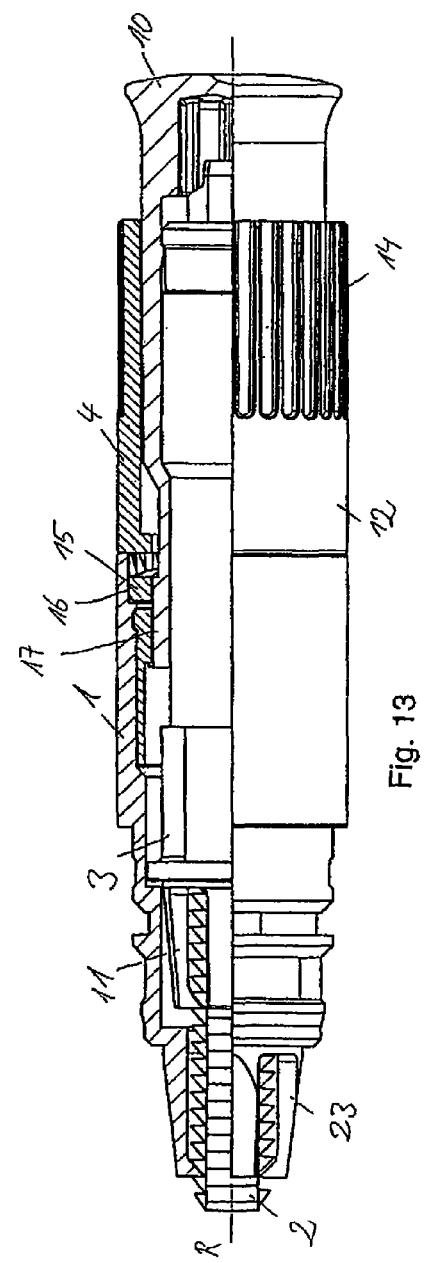

FIG. 13 illustrates the drive and dose metering module as the operating element 10 is being pulled back in the proximal direction. The blocking element 17 is moved into the region of the lock element 15 and therefore blocks the inwardly directed latching movements. A dose can now no longer be set because the dose metering element 4 is locked in both directions of rotation.

Figure 14:
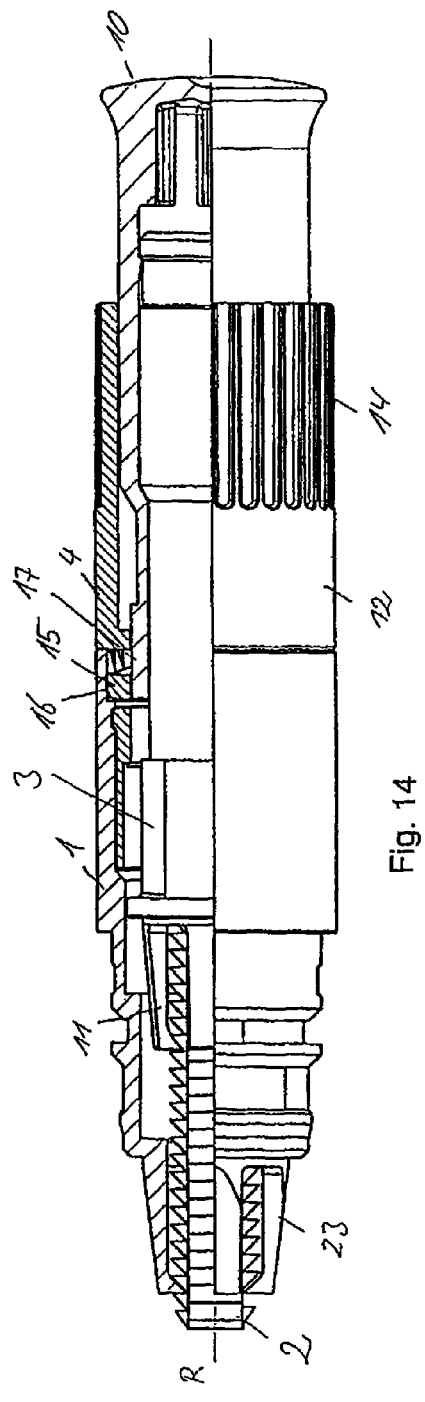

FIG. 14 illustrates the drive and dose metering module in a triggering position, in which the lock element 15 is blocked. Furthermore, because the operating element 10 has been pulled back, the drive element 3 has been driven along by the operating element 10. The drive and dose metering module is now ready for administering the set product dose.

Figure 15:
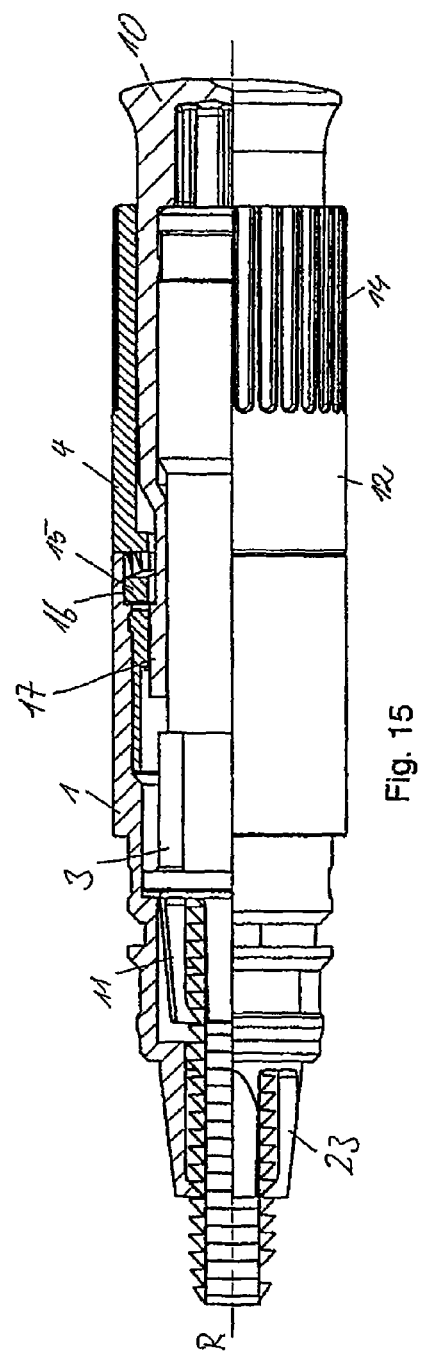

FIG. 15 illustrates the drive and dose metering module in a release position after administering. The output element 2 has been moved in the distal direction depending on the set dose. The lock element 15 has been released by the blocking element 17 again so that a new dose can be set with the dose metering element 4, thereby making it possible to administer another product dose subsequently.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A drive and dose metering module for an injection device, comprising:
   a) a dose metering element moveable relative to a drive element into one of several dose setting positions to set the product dose,
   b) wherein one of the drive element and dose metering element forms several dose setting stops at different axial heights and rotation stops assigned to the dose setting stops,
   c) and the other of the drive element and dose metering element forms at least one selection element,
   d) and wherein the drive element can be moved in translation relative to the dose metering element as far as a triggering position in which the at least one selection element is in abutment with one of the dose setting stops, and
   e) in the triggering position, the at least one selection element locks, by the rotation stops, the rotation of the dose metering element in both directions of rotation.

2. The drive and dose metering module as claimed in claim 1, wherein the dose metering element can be rotated relative to an output element into one of several dose setting positions to set the product dose, and the drive element is mechanically coupled to the output element and can be moved in translation relative to the output element.

3. The drive and dose metering module as claimed in claim 1, wherein the product dose depends on the different axial heights of the several dose setting stops.

4. The drive and dose metering module as claimed in claim 1, wherein the dose setting stops are respectively provided in the form of an end face of a groove extending axially from an end face of the component containing the dose setting stops.

5. The drive and dose metering module as claimed in claim 4, wherein the rotation stops are the sides of the groove.

6. The drive and dose metering module as claimed in claim 5, wherein, on one of the drive element and the dose metering element the dose setting stops are disposed in a stepped arrangement pointing axially towards the other and the sides of the groove form the rotation stops.

7. The drive and dose metering module as claimed in claim 1, wherein the dose setting stops are formed by the dose metering element and the at least one selection element is formed by the output element.

8. The drive and dose metering module as claimed in claim 1, wherein the at least one selection element is a cam or a web extending in the axial direction which projects from a casing surface of the drive element or the dose metering element.

9. The drive and dose metering module as claimed in claim 1, wherein the dose metering element is mechanically coupled to a mechanism holder, wherein the dose metering element can be rotated relative to the mechanism holder.

10. The drive and dose metering module as claimed in claim 1, wherein the drive element is mechanically coupled to a mechanism holder, wherein the drive element can be moved in translation relative to the mechanism holder.

11. The drive and dose metering module as claimed in claim 1, further comprising a conveying mechanism having a manually operable operating element, activation of which causes the conveying movement, and a path length ($H_F+H_L$)

of a movement which can be performed on activation of the operating element is longer than the path length ($H_F$) of the conveying movement corresponding to complete dispensing of the set product dose.

12. The drive and dose metering module as claimed in claim 11, wherein the conveying mechanism has at least one conveying element which is disposed in a reservoir and performs the conveying movement, and in that the operating element is coupled to the conveying element so that it slaves the conveying element across a part ($H_F$) of the path length ($H_F+H_L$) of its movement and travels the other part ($H_L$) of the path length of its movement ($H_F+H_L$) without the conveying element.

13. An injection device comprising a drive and dosing module, wherein the module comprises a dosing member which can be moved into one of several dosing positions in relation to a drive member to set a dose, wherein one of the dosing or drive members forms several dosing stops at axially different heights and rotational stops that are associated with the dosing stops and the other member forms at least one selection element, and wherein the drive member can be moved in relation to the dosing member until it reaches a trigger position in which the at least one selection element attains one of the dosing stops and, in said trigger position, the selection element and the rotational stops combine to lock the rotation of the dosing member in both directions.

14. An injection device for injecting a settable product dose, comprising a drive and dose metering module comprising a dose metering element moveable relative to a drive element into one of several dose setting positions to set the product dose, wherein one of the drive element and dose metering element forms several dose setting stops at different axial heights and rotation stops assigned to the dose setting stops and the other of the drive element and dose metering element forms at least one selection element, and wherein the drive element can be moved in translation relative to the dose metering element as far as a triggering position in which the at least one selection element is in abutment with one of the dose setting stops, and in the triggering position, the at least one selection element locks, by the rotation stops, the rotation of the dose metering element in both directions of rotation.

* * * * *